United States Patent [19]

Power et al.

[11] Patent Number: 5,429,950

[45] Date of Patent: Jul. 4, 1995

[54] HETEROLOGOUS GENE EXPRESSION IN BACILLUS SUBTILIS: FUSION APPROACH

[75] Inventors: Scott D. Power; Johanna M. A. van Kimmenade, both of San Bruno; Louann Carlomagno, Sonoma, all of Calif.

[73] Assignee: Genencor International, Inc., Rochester, N.Y.

[21] Appl. No.: 860,468

[22] Filed: Mar. 30, 1992

[51] Int. Cl.$^6$ .................. C12N 1/20; C12N 9/20; C12N 15/00

[52] U.S. Cl. .................. 435/252.31; 435/198; 435/320.1; 935/38; 935/48; 935/14; 536/23.2; 536/23.4

[58] Field of Search .............. 435/198, 320.1, 252.31, 435/69.1, 221, 222; 935/47, 38, 48, 51; 536/23.2, 23.4

[56] References Cited

U.S. PATENT DOCUMENTS 5,290,694  3/1994  Nakanishi et al. .................. 435/198

FOREIGN PATENT DOCUMENTS 0334462  9/1989  European Pat. Off. .
0464922A1  1/1992  European Pat. Off. .

OTHER PUBLICATIONS

Mountain, A. (1989) Bacillus (C. R. Harwood, ed.), Plenum Press, New York, pp. 73–114.
Stahl et al, *J. Bact.*, vol. 158, No. 2, May 1984, pp. 411–418.

*Primary Examiner*—Robert A. Wax
*Assistant Examiner*—Keith D. Hendricks
*Attorney, Agent, or Firm*—Margaret A. Horn; Christopher L. Stone

[57] ABSTRACT

There are described processes for expressing a lipase in a heterologous host. Further described are transformed cells comprising heterologous DNA and particular plasmids containing heterologous fusion DNA constructs.

24 Claims, 8 Drawing Sheets

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GCAGGCTGCA GGAAAAAGCA                                                20

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

CCACTGTCGC TGCAGGAAAA GCTCCCCTGC                                30

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

GGCTGCCGGA GCTCCCCTGC                                                20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

GCAGGCTGCC GCTCCCCTGC                                                20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

TGCGCAGGCT GCTCCCCTGC                                                20

( 2 ) INFORMATION FOR SEQ ID NO:6:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

CTGCCGGAAA GAGCTCTACA GAAAAG                        26

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

TGTCGCGGCG GAGCTCTACA GAAAAGAAAG CTCCCCTGC           39

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:8:

GTGCCATGAG CTCCGCCAAG A                             21

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:9:

TGTCGCGGCG GAGCTCCGCC AAGAAAAAGG CTCCCCTGC           39

( 2 ) INFORMATION FOR SEQ ID NO:10:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:10:

GGTGTATCCG GCAGGGGAGC GCTTTTTCCG GCAGCCTGCG C          41

( 2 ) INFORMATION FOR SEQ ID NO:11:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:11:

GCGCAGGCTG CCGGAAAAAG CGCTCCCCTG CCGGATACAC C          41

( 2 ) INFORMATION FOR SEQ ID NO:12:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:12:

GGTGTATCCG GCAGGGGAGC ACTGCTTTTT CCGGCAGCCT G          41

( 2 ) INFORMATION FOR SEQ ID NO:13:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:13:

CAGGCTGCCG GAAAAAGCAG TGCTCCCCTG CCGGATACAC C          41

( 2 ) INFORMATION FOR SEQ ID NO:14:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:14:

GGTGTATCCG GCAGGGGAGC TGTACTGCTT TTTCCGGCAG C          41

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:15:

GCTGCCGGAA AAAGCAGTAC AGCTCCCCTG CCGGATACAC C          41

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:16:

GGTGTATCCG GCAGGGGAGC CTTTTCTGTA CTGCTTTTCC          41

( 2 ) INFORMATION FOR SEQ ID NO:17:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:17:

GGAAAAAGCA GTACAGAAAA GGCTCCCCTG CCGGATACAC C         41

( 2 ) INFORMATION FOR SEQ ID NO:18:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

GGTGTATCCG GCAGGGGAGC AATGTATTTC TTTTCTGTAC T         41

( 2 ) INFORMATION FOR SEQ ID NO:19:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:19:

AGTACAGAAA AGAAATACAT TGCTCCCCTG CCGGATACAC C         41

( 2 ) INFORMATION FOR SEQ ID NO:20:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

AAGCCTATGA ATTCCTCCAT TTTCTTCT                         28

( 2 ) INFORMATION FOR SEQ ID NO:21:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

TTCCCGCCCG GTACCGGCAT TGG                              23

( 2 ) INFORMATION FOR SEQ ID NO:22:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear (ii) MOLECULE TYPE: DNA (genomic)

(xi) SEQUENCE DESCRIPTION: SEQ ID NO:22:

GGTGTATCCG GCAGGGGAGC TTCTGTACTG CTTTTTCCGG C　　41

(2) INFORMATION FOR SEQ ID NO:23:

(i) SEQUENCE CHARACTERISTICS:
        (A) LENGTH: 41 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:23:

GCCGGAAAAA GCAGTACAGA AGCTCCCCTG CCGGATACAC C　　41

HETEROLOGOUS GENE EXPRESSION IN BACILLUS SUBTILIS: FUSION APPROACH

CROSS-REFERENCE TO RELATED APPLICATIONS

This application is related to U.S. application Ser. No. 07/800,365 filed Nov. 27, 1991, which is a continuation-in-part of U.S. application Ser. No. 07/600,836 filed Oct. 22, 1990, which is a continuation of U.S. patent application Ser. No. 07/341,200 filed Mar. 29, 1989, now U.S. Pat. No. 4,981,611, which, in turn, is derived from PCT Application Serial No. PCT/US88/01844 filed May 31, 1988, which, in turn, claims priority under 35 USC §120 from U.S. patent application Ser. No. 07/056,500 filed May 29, 1987 (now abandoned). Each of the above applications are incorporated herein by reference in their entirety.

1. Field of the Invention

The present invention relates to the expression of lipase (cutinase) from Bacillus microorganisms and the purification of cutinase from the fermentation broth.

2. Background of the Invention

The secretion of heterologous proteins from any host requires the precise matching of signal peptide and mature target gene. Although gram-positive signal sequences are known to function well in gram-negative systems, the inverse is not true [Mountain, A. (1989) *Bacillus* (Biotechnology Handbooks 2, C. R. Harwood, ed.), Plenum Press, pp. 73–114]. In the case of *Bacillus subtilis*, it has been possible to secrete proteins derived from other gram-positive organisms; however, even in these situations, the best yields have been obtained with hybrid sequences. There has been no documented success in *Bacillus* for expressing large quantities of gram-negative derived proteins utilizing their own signal sequences; in addition, success with hybrid sequences has been minimal. [Mountain, A. (1989) *Bacillus* (Biotechnology Handbooks 2, C. R. Harwood, ed.), Plenum Press, pp. 73–114.]

There have been various attempts in the literature to optimize signal peptide: mature gene fusions (cf. Doi, R. H., Wong, S. and Kawamura, F. (1986) Trends Biotechnol. September:232–235; Fahnestock, S. R. and Fisher, K. E. (1986) J. Bact. 165:796–804; Fahnestock, S. R. and Fisher, K. E. (1987) Appl. Env. Microbiol. 53:379–384; Sarvas, M. (1986) Curr. TopicsMicro. Immun. 125:103–125; Ulmanen, I., Lundstrom, K., Lehtovaara, P., Sarvas, M., Ruohonen, M. and Palva, I. (1985) J. Bact. 162:176–182; Vasantha, N. and Thompson, L. D. (1986) J. Bact. 165:837–842); however, in all cases, the points of fusion were chosen on the basis of either convenient restriction sites or by merely mating the gram-positive signal sequence to the target gene directly at the signal cleavage site.

The present invention describes the expression of the gram-negative *Pseudomonas mendocina* lipase (cutinase) in *Bacillus subtilis*, a gram-positive organism. The enzyme is produced as a fusion with aprE (prepro *Bacillus subtilis* subtilisin). Using polymerase chain reaction techniques, the mature coding sequence for lipase, as described in commonly owned U.S. application Ser. No. 07/932,950 incorporated herein by reference, was fused to the prosequence of aprE at (and including) prosequence residues A(−1), A1, G2, K3, S4, S5, T6, E7, K8, K9, I11 and K27. The resulting constructions were integrated into the chromosome of a *Bacillus subtilis* production host (BB8) and after transduction or transformation to SacU(Hy) phenotype, the production efficiency of each strain was measured as described herein.

SUMMARY OF THE INVENTION

The present invention relates to the expression of heterologous genes in a Bacillus microorganism wherein one or more fusions are sequentially made, said fusions comprising a host signal sequence, a host pro sequence and a target gene sequence.

Further provided is the expression of lipase (cutinase) in Bacillus using a promotor derived from *Bacillus subtilis* and terminator derived from *Bacillus amyloliquefaciens*.

Still further provided are specific fusions of the mature lipase gene with the *Bacillus subtilis* aprE gene. These specific fusions may be introduced into plasmid vectors which are then transformed into *B. subtilis*.

BRIEF DESCRIPTION OF THE DRAWINGS

FIG. 4 describes the construction of: (FIG. 4a) pAprcut-1; (FIG. 4b) pAK-K3; (FIG. 4c) pAK-G2, pAK-A1, pAK-A(−1); (FIG. 4d) pAK-K9, pAK-K27; (FIG. 4e) pAK-S4, S5, T6, E7, K8, I11.

DETAILED DESCRIPTION OF THE PRESENT INVENTION

A. Secretion of Proteins from Bacteria

Figure 1:
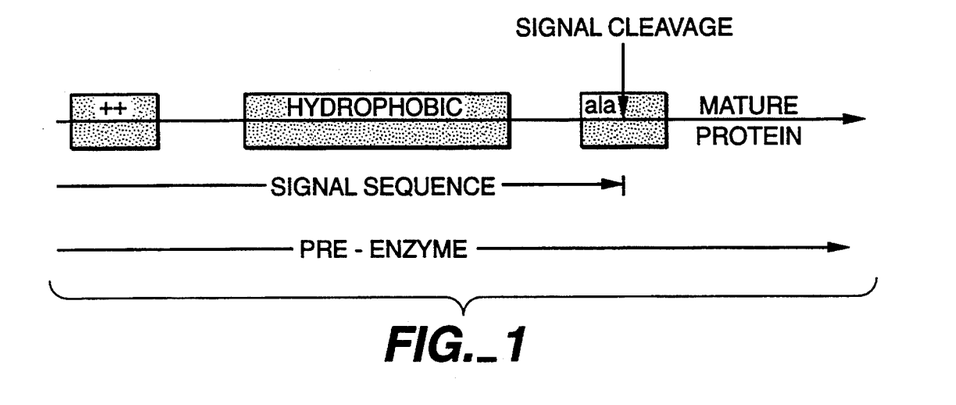
FIG. 1 shows the key elements of signal sequence secondary structure.

The secretion of proteins from bacteria is an ATP-dependent process which involves the translocation of a pre-protein and the subsequent proeolytic cleavage of the pre-protein on the outside surface of the membrane, into the mature enzyme. The pre-protein consists of an N-terminal, signal peptide of 20 (gram-negative) to 40 amino acids [Mountain, A. (1989) *Bacillus* (C. R. Harwood, ed.), Plenum, N.Y., 73–114] and a C-terminal mature protein. Signal sequences exhibit only restricted, if any primary sequence homology, even within a single organism, yet conserve secondary structural homology as shown in FIG. 1. The three domains of the signal peptide are first the N-terminal, positively charged region, the hydrophobic central region, and the non-helical, carboxy terminal domain. As will be discussed below, gram-positive organisms tend to have larger N and C-terminal domains than those of gram-negative organisms, such as *E. coli*, maintaining the central hydrophobic core of approximately the same length. This signal sequence is thought to contain all of the information necessary to target the protein to the membrane for translocation. [See: Mountain, A. (1989) *Bacillus* (C. R. Harwood, ed.), Plenum, N.Y., 73–114; Wickner, W., Driessen, A. J. M. and Hartl, F. U. (1991) Annu. Rev. Biochem. 60:101–124; Schatz, P. J. and Beckwith, J. (1983) J. Bacteriol. 154:253–260.]

In the first step of secretion, as documented for the gram-negative *E. coli*, the newly synthesized pre-protein, potentially with a chaperonin (secB, groEL, etc.), is thought to be recognized by the membrane bound receptor ATP-ase (secA), which couples the hydrolysis of ATP to the translocation of the protein through an integral membrane complex (secE/Y) [cf. Mountain, A. (1989) *Bacillus* (C. R. Harwood, ed. ) , Plenum, N.Y., 73–114; Wickner, W., Driessen, A. J. M. and Hartl, F. U. (1991) Annu. Rev. Biochem. 60:101–124; Schatz, P. J. and Beckwith, J. (1990) Annu. Rev. Genet. 24:215–248 and references therein]. A key feature of the pre-enzyme is that it must be in a translocation-competent form, perhaps loosely folded, which can be maintained via an interaction with chaperonin proteins [see: Wickner, W., Driessen, A. J. M. and Hartl, F. U. (1991) Annu. Rev. Biochem. 60:101–124; Kumamoto, C. A., and Beckwith, J. (1983) J. Bacteriol. 154:253–260; Kumamoto, C. A. and Nault, A. K. (1989) Gene 75:167–175.] It is this complex which must contain all of the information for the recognition and translocation of a protein by the secretory apparatus. One potential role of the signal sequence may be in facilitating chaperonin binding by preventing folding of the enzyme into its final mature form [Park, S., Liu, G., Topping, T. B., Cover, W. H. and Randall, L. L. (1988) Science 239:1033–1035; Laminet, A. A. and Pluckthun, A. (1989) EMBO J. 8:1469–1477].

B. Heterologous Secretion in Gram-Positive Organisms

Although secretion in *Bacillus subtilis* is not as well understood as secretion in *E. coli*, it is generally assumed that it proceeds by the same mechanism [Saier, M. H., Jr., Werner, P. K. and Muller, M. (1989) Microbiol. Rev 53:333–366; Overhoff, B., Klein, M., Spies, M. and Freudl, R. (1991) Mol. Gen. Genet. 228:417–423]. One difference between the two sets of secreted proteins is the length of their signal peptides which tend to be up to 20 amino acids longer in gram-positives than their corresponding gram-negative counterparts. Whereas gram-positive signal peptides function in gram-negative systems, the converse is not true [Mountain, A. (1989) *Bacillus* (C. Harwood, ed.), Plenum Press, N.Y., 73–114; Borchert, T. V. and Nagarajan, V. (1991) J. Bacteriol. 173:276–282; Perlman, D. and Halvorson, H. O. (1983) J. Mol. Biol. 167:391–409]. Thus, the general strategy for the expression of heterologous proteins in gram-positive organisms such as *Bacillus subtilis* has involved mating the target protein to the secretory apparatus of the host (for a review see Mountain, A. (1989) *Bacillus* (C. Harwood, ed. ) , Plenum Press, New York, 73–114). Typically, in successful experiments, investigators have mated a major exoenzyme promoter and signal sequence to the mature domain of the target. Such systems have been devised for *Bacillus subtilis* employing elements from alpha amylase (Shiroza, T., Nakazawa, K., Tashiro, N., Yamane, K., Yanagi, K., Yamasaki, M., Tamura, G., Saito, H., Kawade, Y. and Taniguchi, T. (1985) Gene 34:1–8; Yamane, K., Nakazawa, K., Nakamura, K., Minekura, H., Mori, T., Takano, J., Shiroza, T., Sohma, A. and Fujita, T. (1986) in Bacillus Molecular Genetics and Biotechnology Applications (A. T. Ganesan and J. A. Hochs eds.) Academic Press, New York, pp. 411–422; Palva, I. (1982) Gene 19:81–87; Ulmanen, I., Lundstrom, K., Lehtovaara, P., Sarvas, M., Ruohonen, M. and Palva, I. (1985) J. Bacteriol. 162:176–182) , alkaline and neutral protease (Fahnestock, S. R. and Fisher, K. E. (1986) J. Bacteriol. 165:796–804; Vasantha, N. and Thompson, L. D. (1986) J. Bacteriol. 165:837–842; Wong, S. L., Kawamura, F. and Doi, R. H. (1986) J. Bacteriol. 168:1005–1009) , beta lactamase (Chang, S., Gray, O., Ho, D., Kroyer, J., Chang, S. Y., McLaughlin, J. and Mark, D. (1984) in Molecular Cloning and Gene Regulation in Bacilli, pp. 159–169) and levansucrase (Borchert, T. V. and Nagarajan, V. (1991) J. Bacteriol. 173:276–282). In positioning the fusion of the donor promoter/signal sequence with the mature target gene, the investigators have typically considered the linear organization of signal peptide, peptide cleavage site and mature gene and have most often linked the target to the donor signal sequence directly at the proteolytic junction (see FIG. 1) or just after it, adding at most one or two amino acids from the mature gene of the signal sequence donor (see Mountain, A. (1989) *Bacillus* (C. Harwood, ed. ) , Plenum Press, New York, 73–114 and references therein). In general, the results have been mediocre, with accumulation levels of non-gram-positive, heterologous proteins seldom exceeding mg/L amounts (Mountain, A. (1989) *Bacillus* (C. Harwood, ed.), Plenum Press, New York, 73–114).

These methods do not take into account a possible association of the signal peptide with the mature protein. As discussed above, one possible role of the signal peptide is to facilitate binding of the required chaperonins prior to acquisition and translocation by the secretory apparatus. As a consequence of this requirement as well as other possible structures required for efficient translocation, the signal peptide may be required to interact specifically with the mature protein. This has been suggested most conclusively by the work of Lehnhardt and coworkers who demonstrated that different mature sequences (TEM beta-lactamase and *Staphylococcus aureus* nuclease A) worked in very different ways with the same heterologous signal (OmpA) and its variants in *E. coli* (Lenhardt, S., Pollitt, S. and Inouye, M. (1987) J. Biol. Chem. 262:1716–1719). In addition, Breitling and coworkers have made similar observations in the secretion of human interferon alpha 1 in *Bacillus subtilis* using staphylokinase and *Bacillus subtilis* alpha amylase secretion vectors (Breitling, R., Gerlach, D., Hartmann, M. and Behnke, D. (1989) Mol. Gen. Genet 217:384–391). Despite the observations described, no one has attempted to optimize heterologous secretion through systematically changing the fusion junction between the donor gene and the target mature gene.

Experimental

Although the following examples are all related to the expression of *Pseudomonas mendocina* ATCC 53552 lipase (cutinase) in *Bacillus subtilis*, the examples are offered merely to illustrate the present invention and should not be construed in any way as limiting the scope of this invention.

In this example, the expression of *Pseudomonas mendocina* lipase (cutinase) as described in commonly owned U.S. Pat. No. 4,933,287, incorporated herein by reference, in *Bacillus subtilis* is carried out through the fusion of the mature lipase gene with the *Bacillus subtilis* aprE gene from the last residue of the signal sequence (Ala-1) through the ninth residue of the aprE prosequence (K9). In addition, fusions at positions I11 and K27 were also obtained.

Nomenclature:

In this example, the full length, mature gene for the *Pseudomonas mendocina* lipase (cutinase) described in U.S. Ser. No. 932,950, filed Nov. 19, 1986, incorporated herein by reference, has been fused in frame to several positions within the *Bacillus subtilis* aprE promoter/signal/prosequence. The aprE, signal/pro sequence junction occurs between codons 29(Ala) and 30(Ala). The fusion of the mature lipase (cutinase) to aprE codon 29 is thus called pAK-A(−1) indicating that the lipase (cutinase) has been fused to the last residue of the signal peptide. Likewise, the fusion of mature lipase (cutinase) to aprE codon 30 is called pAK-A1 indicating that the lipase (cutinase) has been fused to the first residue of the prosequence.

Construction of aprE/Lipase (Cutinase) Fusions

The following synthetic primers were used for the mutagenesis:

| | | |
|---|---|---|
| 1A. | 5' GCAGGCTGCAGGAAAAAGCA 3' | Seq ID No: 1 |
| B. | 5' CCACTGTCGCTGCAGGAAAAGCTCCCCTGC 3' | Seq ID No: 2 |
| 2. | 5' GGCTGCCGGAGCTCCCCTGC 3' | Seq ID No: 3 |
| 3. | 5' GCAGGCTGCCGCTCCCCTGC 3' | Seq ID No: 4 |
| 4. | 5' TGCGCAGGCTGCTCCCCTGC 3' | Seq ID No: 5 |
| 6A. | 5' CTGCCGGAAAGAGCTCTACAGAAAAG 3' | Seq ID No: 6 |
| B. | 5' TGTCGCGGCGGAGCTCTACAGAAAAGAAAGCTCCCCTGC 3' | Seq ID No: 7 |
| 7A. | 5' GTGCCATGAGCTCCGCCAAGA 3' | Seq ID No: 8 |
| B. | 5' TGTCGCGGCGGAGCTCCGCCAAGAAAAAGGCTCCCCTGC 3' | Seq ID No: 9 |
| 8A. | 5' GGTGTATCCGGCAGGGGAGCGCTTTTTCCGGCAGCCTGCGC 3' | Seq ID No: 10 |
| B. | 5' GCGCAGGCTGCCGGAAAAAGCGCTCCCCTGCCGGATACACC 3' | Seq ID No: 11 |
| 9A. | 5' GGTGTATCCGGCAGGGGAGCACTGCTTTTTCCGGCAGCCTG 3' | Seq ID No: 12 |
| B. | 5' CAGGCTGCCGGAAAAAGCAGTGCTCCCCTGCCGGATACACC 3' | Seq ID No: 13 |
| 10A. | 5' GGTGTATCCGGCAGGGGAGCTGTACTGCTTTTTCCGGCAGC 3' | Seq ID No: 14 |
| B. | 5' GCTGCCGGAAAAAGCAGTACAGCTCCCCTGCCGGATACACC 3' | Seq ID No: 15 |
| 11A. | 5' GGTGTATCCGGCAGGGGAGCCTTTTCTGTACTGCTTTTTCC 3' | Seq ID No: 16 |
| B. | 5' GGAAAAAGCAGTACAGAAAAGGCTCCCCTGCCGGATACACC 3' | Seq ID No: 17 |
| 12A. | 5' GGTGTATCCGGCAGGGGAGCAATGTATTTCTTTTCTGTACT 3' | Seq ID No: 18 |
| B. | 5' AGTACAGAAAAGAAATACATTGCTCCCCTGCCGGATACACC 3' | Seq ID No: 19 |
| 13. | 5' AAGCCTATGAATTCCTCCATTTTCTTCT 3' | Seq ID No: 20 |
| 14. | 5' TTCCCGCCCGGTACCGGCATTGG 3' | Seq ID No: 21 |
| 15A. | 5' GGTGTATCCGGCAGGGGAGCTTCTGTACTGCTTTTTCCGGC 3' | Seq ID No: 22 |
| B. | 5' GCCGGAAAAAGCAGTACAGAAGCTCCCCTGCCGGATACACC 3' | Seq ID No: 23 |

Construction of fusion K3:

The lipase (cutinase) gene (as described in U.S. Pat. Nos. 4,933,287 and 5,030,240 and U.S. patent application Ser. No. 629,308, all incorporated herein by reference) was cloned into a M13 plasmid as a HindIII SphI fragment (M13lip); a PstI site and three codons (A,G,K) were introduced at the beginning of the mature coding sequence by site-directed mutagenesis (T. A. Kunkel, PNAS (1985), Vol. 82, pp. 488–492) using single-stranded synthetic primer 1B (Seq ID No: 2). The aprE gene from pS168-1 (M. L. Stahl, et. al., J. Bact. (1984), Vol. 158, pp. 411–418) was cloned into another M13 plasmid as an EcoRI-HindIII fragment (M13apr) and a PstI site was introduced at codon position Ala1 (first amino acid following the signal sequence cleavage site) with single-stranded synthetic primer 1A (Seq ID No: 1) using the same technique. The method of cloning the DNA fragments is provided in Sambrook, et al., Molecular Cloning, a Laboratory Manual (1989) pp. 1.53–1.73 and pp. 4.3–4.51. The EcoRI-PstI fragment of aprE and the PstI-SphI fragment of lipase were isolated from the M13 plasmids and cloned into EcoRI SphI digested pJM102 (E. Ferrari, et al., J. Bact. (1983) Vol. 154, pp. 1513–1515), creating pApr-cut-1.

To introduce a strong transcriptional terminator, the aprE-lipase fusion from pApr-cut-1 was cloned into pJH101 (E. Ferrari, et al., J. Bact. Vol. 154, pp. 1513–1515) which had been constructed to contain the Bacillus amyloliquefaciens subtilisin transcriptional terminator (Wells, et al., Nucleic Acid Research (1983), Vol. 11, pp. 7911–7925 on a HindIII-BamHI fragment (pJH101-term)). The EcoRI-PvuII DNA fragment containing the aprE promoter, signal sequence and the 5' end of the lipase gene and the PvuII-AvaI DNA fragment containing the 3' end of the lipase gene were isolated from pApr-cut-1. The AvaI5' overhang of the PvuII-AvaI fragment of the lipase gene was filled in by T4 polymerase prior to the PvuII digest (Sambrook, et al., Molecular Cloning, a Laboratory Manual, ibid). The plasmid pJH101-term (with the terminator) was digested with EcoRI-HindIII and the HindIII 5' overhang was also filled in with T4 polymerase prior to the EcoRI digest. The EcoRI-PvuII fragment, the PvuII-AvaI fragment and the EcoRI-HindIII digested vector were ligated to create pAK-K3.

Construction of fusions G2, A1 and A(−1).

The EcoRI-Asp718 DNA fragment from pAK-K3 was cloned into an M13 plasmid and the codons coding for K, the 3rd amino acid of the prosequence of aprE (K3), G and K, the 2nd and 3rd amino acid of the prosequence of aprE (G2-K3) and A, G and K, the 1st, 2nd and 3rd amino acid of the prosequence of aprE (A1-G2-K3) were deleted by site-directed mutagenesis using the single-stranded synthetic primers 2,3 and 4 respectively (Seq ID Nos: 3, 4 and 5 respectively). The EcoRI-Asp718 fragments from the M13 plasmids containing the deletions were cloned into EcoRI-Asp718 digested pAK-K3 vector, constructing pAK-G2, pAK-A1 and pAK-A(−1) respectively.

Construction of fusion K9.

The lipase (cutinase) gene was cloned into an M13 plasmid as an HindIII- SphI fragment (M13lip) and five codons (S, T, E, K, K) and a SacI site were introduced in front of the mature lipase gene using primer 6B (Seq ID No: 7) in the mutagenesis procedure. The aprE gene from pS168-1 (M. L. Stahl, et. al., J. Bact. (1984), Vol. 158, pp. 411–418) was cloned into another M13 plasmid as an EcoRI-HindIII fragment (M13apr) and a SacI site was introduced within codons 3-5 of the aprE prosequence (K3-S4-S5), using the oligonucleotide primer 6A (Seq ID No: 6) in the mutagenesis procedure.

The resulting EcoRI-SacI fragment of the aprE gene and the SacI-Asp718 fragment of lipase (cutinase) were isolated from the M13 plasmids and cloned into EcoRI-Asp718 digested pAK-K3 vector. The resulting plasmid (AK-K9) contains the mature lipase (cutinase) gene fused to the 9th amino acid (K9) in the prosequence of the aprE gene.

Construction of fusion K27.

This fusion was made using the same procedure using the same M13 plasmids as described above For the K9 fusion. The SacI site was introduced at the 22nd codon of the prosequence of aprE (S22) using single-stranded synthetic primer 7A (Seq ID No: 8). Five codons (S, A, K, K, K) and a SacI site were introduced in front of the mature lipase gene using single-stranded synthetic primer 7B (Seq ID No: 9).

The resulting EcoRI-SacI fragment of the aprE gene and the SacI-Asp718 fragment of lipase (cutinase) were isolated from the M13 plasmids and cloned into an EcoRI-Asp718 digested pAK-K3 vector. The resulting plasmid (AK-K27) contains the mature lipase (cutinase) gene fused to the 27th amino acid (K27) in the prosequence of the aprE gene.

Construction of fusions S4, S5, T6, E7, K8 and I11

These constructions were made by the fusion PCR method (R. M. Horton, et.al. (1989) Gene Vol. 77, pp. 61–68). The polymerase chain reaction (PCR) was carried out in 100 ul PCR buffer (Perkin Elmer/Cetus) with 50 pmol of each primer and 2.5 units of Taq polymerase (Perkin Elmer/Cetus). The reaction mixture was covered with mineral oil to prevent evaporation. The temperature program consisted of:

1 cycle of 10 min. 95 C., 1 min. 50 C., 1 min. 70 C.
28 cycles of 1 min. 95 C., 1 min. 50 C., 1 min. 70 C.
1 cycle of 1 min. 95 C., 1 min. 50 C., 15 min. 70 C.

Two complementary single-stranded synthetic DNA strands coding for the fusion junction were synthesized for each construction, containing the 21 bp of the upstream aprE gene sequence followed by the 20 bp of the downstream lipase (cutinase) gene sequence. Primer 13 (Seq ID No: 20), a single-stranded synthetic primer which codes for the positive strand, is complementary to the aprE promoter and contains an EcoRI site. Primer 14 (Seq ID No: 21), a single-stranded synthetic primer which codes for the negative strand, is complementary to the lipase (cutinase) gene and contains an Asp718 site. Primers 13 (Seq ID No: 20) and 14 (Seq ID No: 21) were used in all constructions.

A set of three PCR reactions were done as follows. DNA between the promoter and fusion point was amplified using primer 13 (Seq ID No: 20) and the single-stranded synthetic primer coding for the negative strand of the fusion junction (A); the template was an EcoRI-HindIII fragment from pS168-1, containing the aprE promoter, signal sequence, pro sequence and the 5' of the mature gene (reaction 1). The DNA between the fusion point and mature lipase gene was amplified using primer 14 (Seq ID No: 21) and the single-stranded synthetic primer coding for the positive strand of the fusion junction (B); the template was a 1:100 dilution of a standard DNA miniscreen of plasmid pAK-K3 (reaction 2). The DNA fragments from reaction 1 were fused to the DNA fragments from reaction 2 by amplification with primers 13 (Seq ID No: 20) and 14 (Seq ID No: 21), using 1 ul of each reaction 1 and 2 (reaction 3). After 30 cycles half of the amplified DNA was cleaned with phenol/chloroform extraction, followed by spin-column purification (Worthington Mini-Spin) according to the manufacturer's directions. The EcoRI-Asp718 fragments were isolated from the amplified DNA and cloned into M13-mp19 EcoRI-ASp718 digested vector. After sequence confirmation (Sanger, et al., 1977) the EcoRI-Asp718 fragments were cloned into EcoRI-Asp718 digested pAK-K3 vector.

The A and B pairs of fusion primers used for the S4, S5, T6, K8, I11 and E7 constructions were numbers 8A&B, 9A&B, 10A&B, 11A&B, 12A&B and 15A&B respectively (Seq ID Nos: 10–19 and 22 and 23 respectively).

Transformation into *Bacillus subtilis*

The plasmids containing the different fusions were transformed into *Bacillus subtilis* (Anagnostopoulos, C., J. Bact. (1961) 81:741–746) and integrated into the chromosome specifically within the aprE locus by a Campbell-type mechanism (Young, M., J. Gen. Microbiol. (1984) 130:1613–1621). The Bacillus strain (BB8) was a derivative of I168 which had been deleted for 5 proteases, and estB (delta apr, delta npr, delta bpF, delta epr, isp-1, delta estB). Deletion of the genes indicated were introduced using the method as described n Stahl, M. L., J. Bact. (1984) 158:411–418. After transformation with the fusion gene, the sacU(Hy) (Henner, D. J., Ferrari, E., Perego, M. and Hoch, J. A., J. Bact. (1988) 170:296–300) mutation was introduced by either transformation or PBS-1 mediated transduction (Hoch, J. A., Barat, M. and Anagnostopoulos, C., J. Bact. (1983) 154:1513–1515) creating the different final *Bacillus subtilis* strains carrying the different fusions.

Cultivation and Evaluation of aprE/Lipase Fusion Strains

The final *Bacillus subtilis* strains were assayed for the production of lipase (cutinase) in the culture supernatant using the following assay:

Assay: *Pseudomonas mendocina* lipase (cutinase) is assayed with 1 mM p-nitrophenylbutyrate in 0.2M Hepes buffer at pH 7.0. The activity is expressed as change in absorbance at 410 nm/min/10 ul sample in a 1 mL reaction volume; 1 unit=a change of 1AU410-/min/10 uL sample in a 1 mL reaction volume. The results were converted to mg/ml based upon a specific activity of 0.060 (mg/mL)/Unit.

Figure 2:
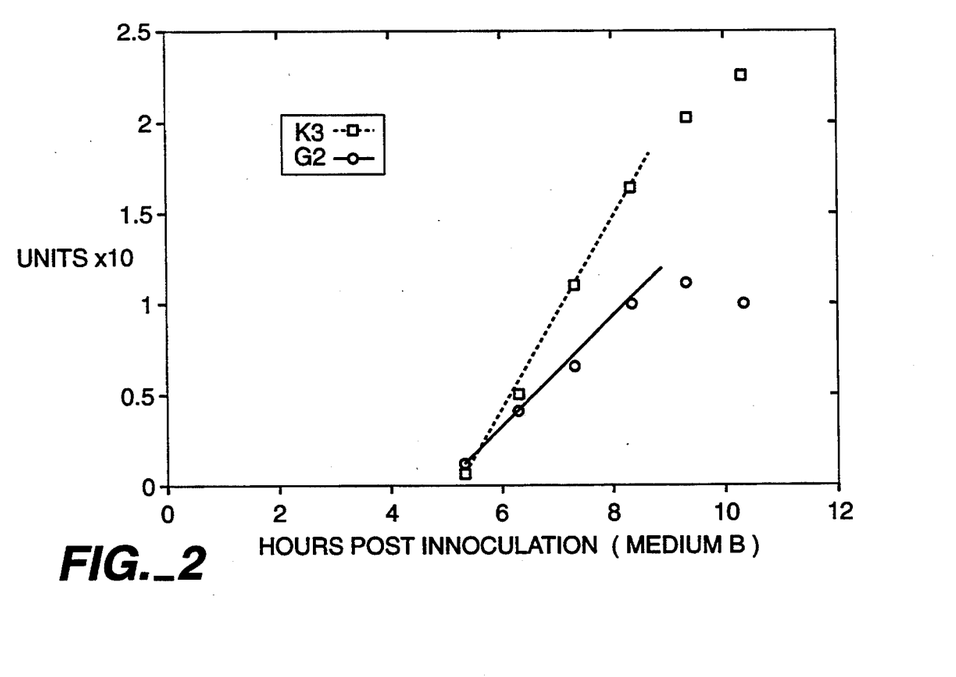
FIG. 2 shows lipase production rate of certain fusions (G2 and K3) in *B. subtilis*.

The Bacillus strains were grown overnight in Medium A at 37° C. with shaking and then inoculated 5% into Medium B and the production of lipase (cutinase) followed using the above assay. Mediums A and B are described in Table I. The strains were evaluated on the basis of their production rate over the initial linear production interval (FIG. 2) and expressed as mg/mL/hr.

TABLE I

| Medium A | |
|---|---|
| Penassay broth (Difco) | |
| Medium B | |
| Nutrient broth (Difco) | 0.8% |
| CaCl$_2$ | 1 mM |
| FeSO$_4$ | 0.001 mM |
| MnCl$_2$ | 0.01 mM |
| KCl | 0.1% |
| MgSO$_4$ | 0.025% |
| Maltodextrin (CPC M150) | 0.1% |

Figure 3:
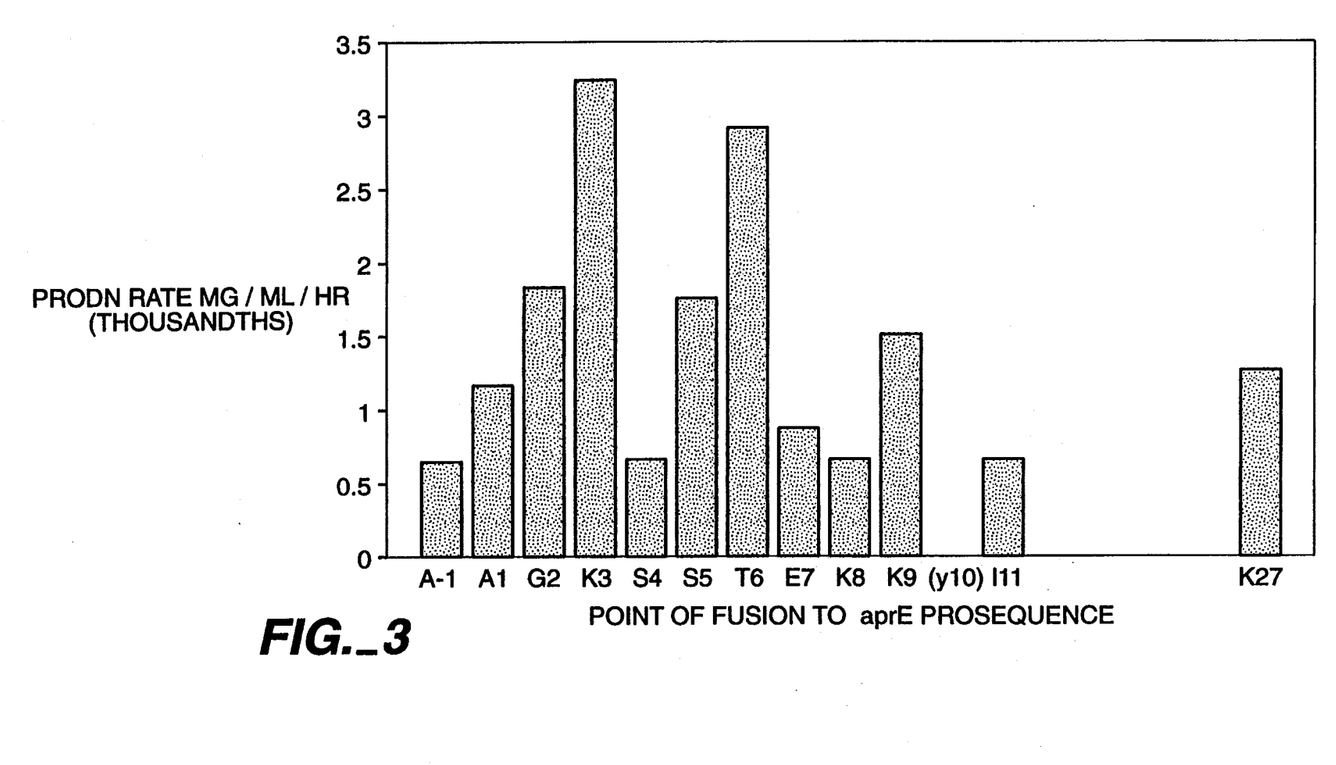
FIG. 3 shows expression of *Pseudomonas mendocina* lipase (cutinase) in *B. subtilis*.
Figure 4A:
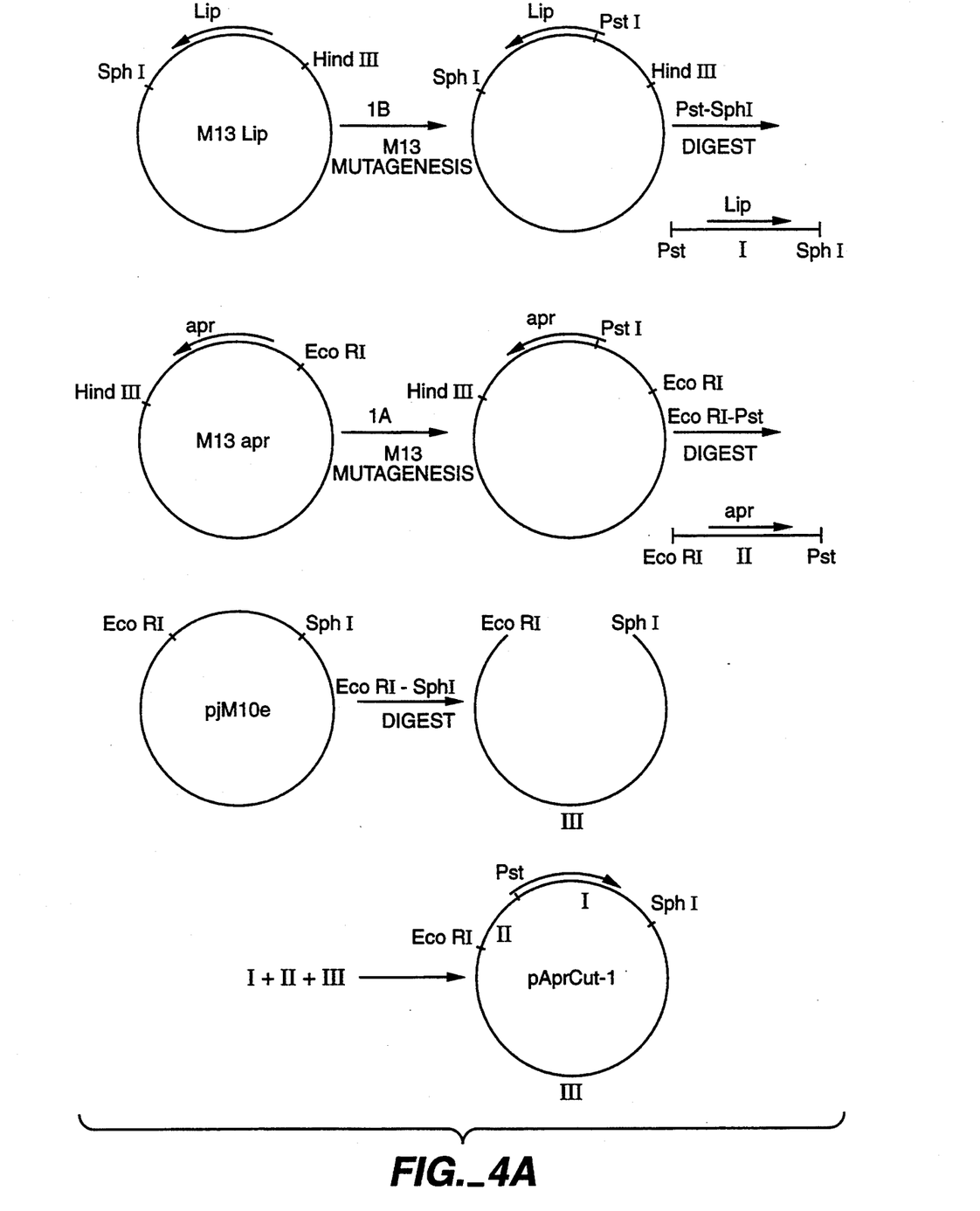
Figure 4B:
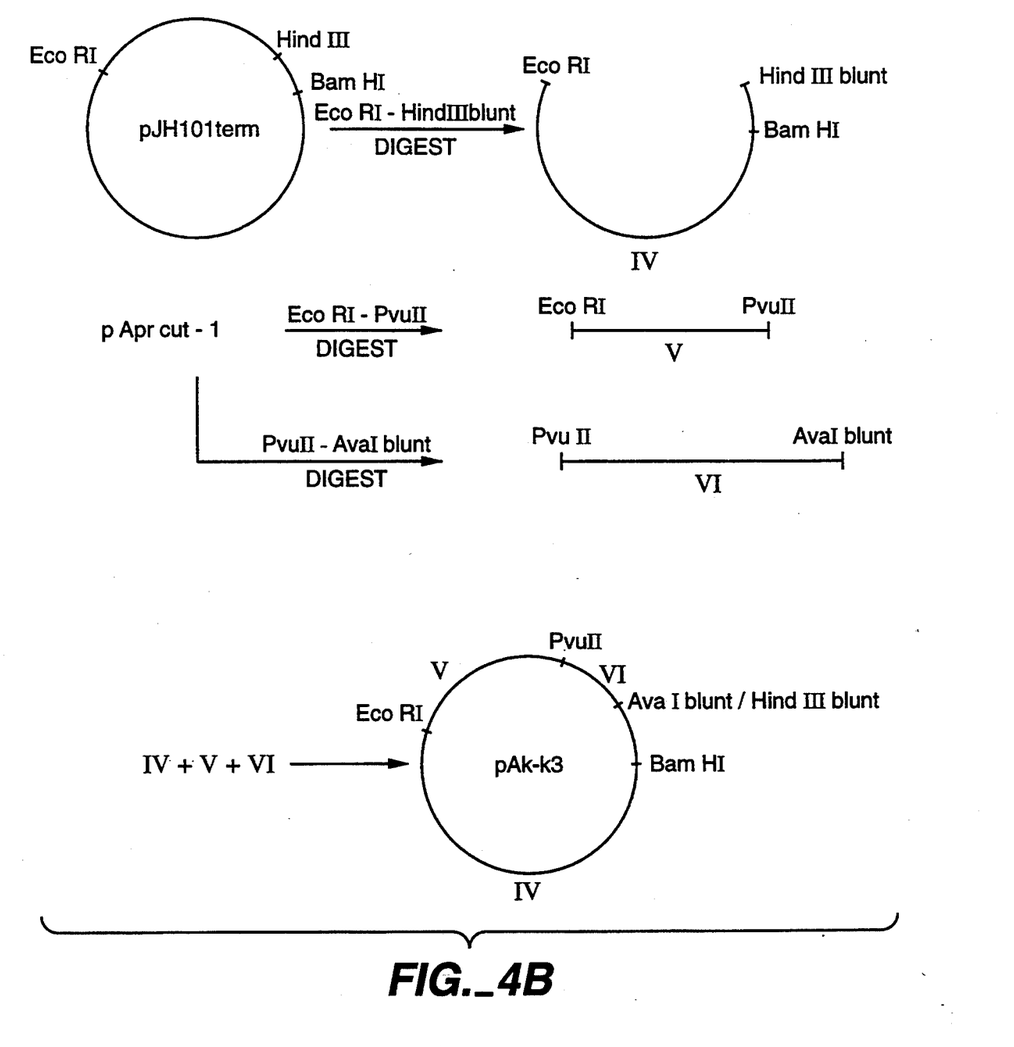
Figure 4C:
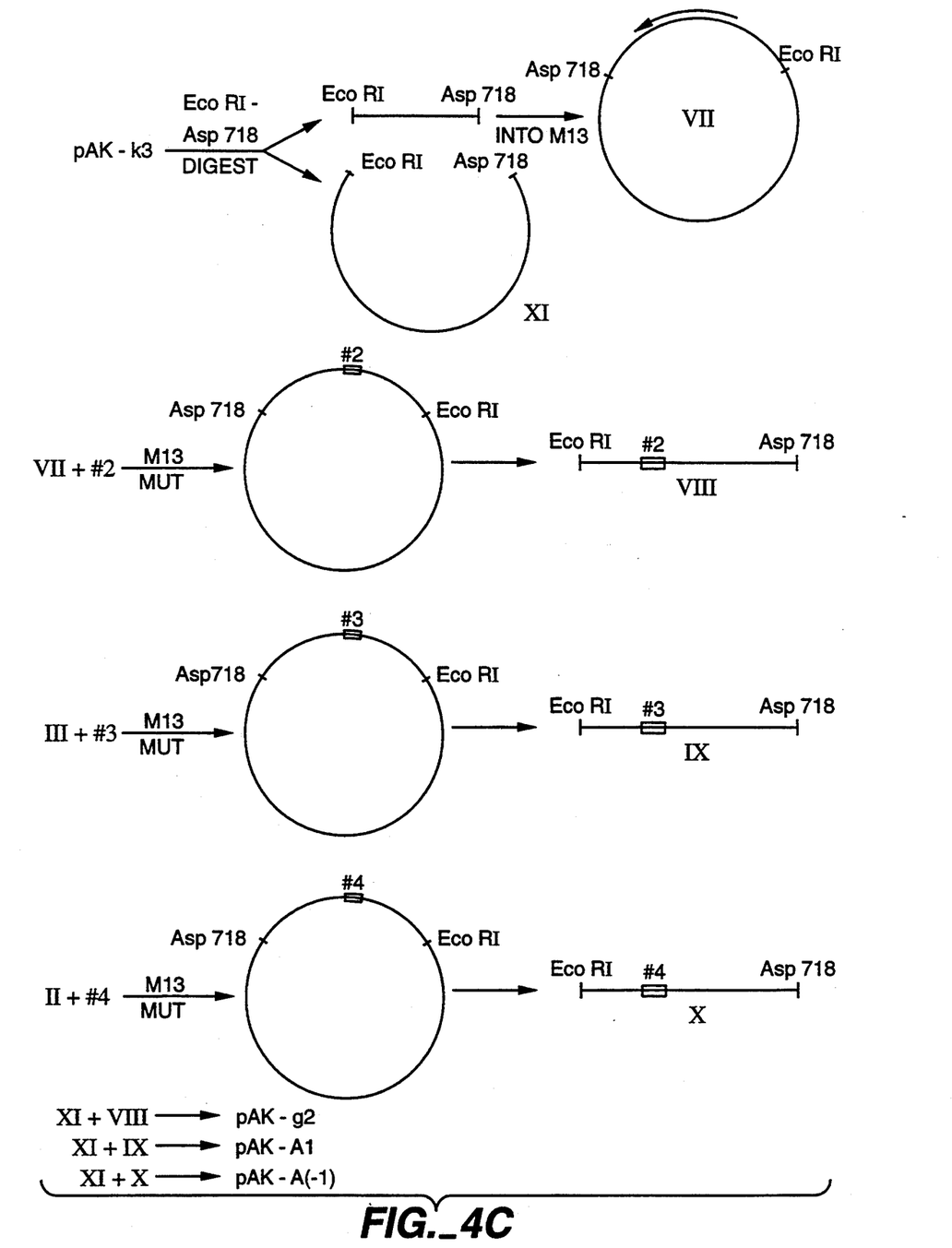
Figure 4D:
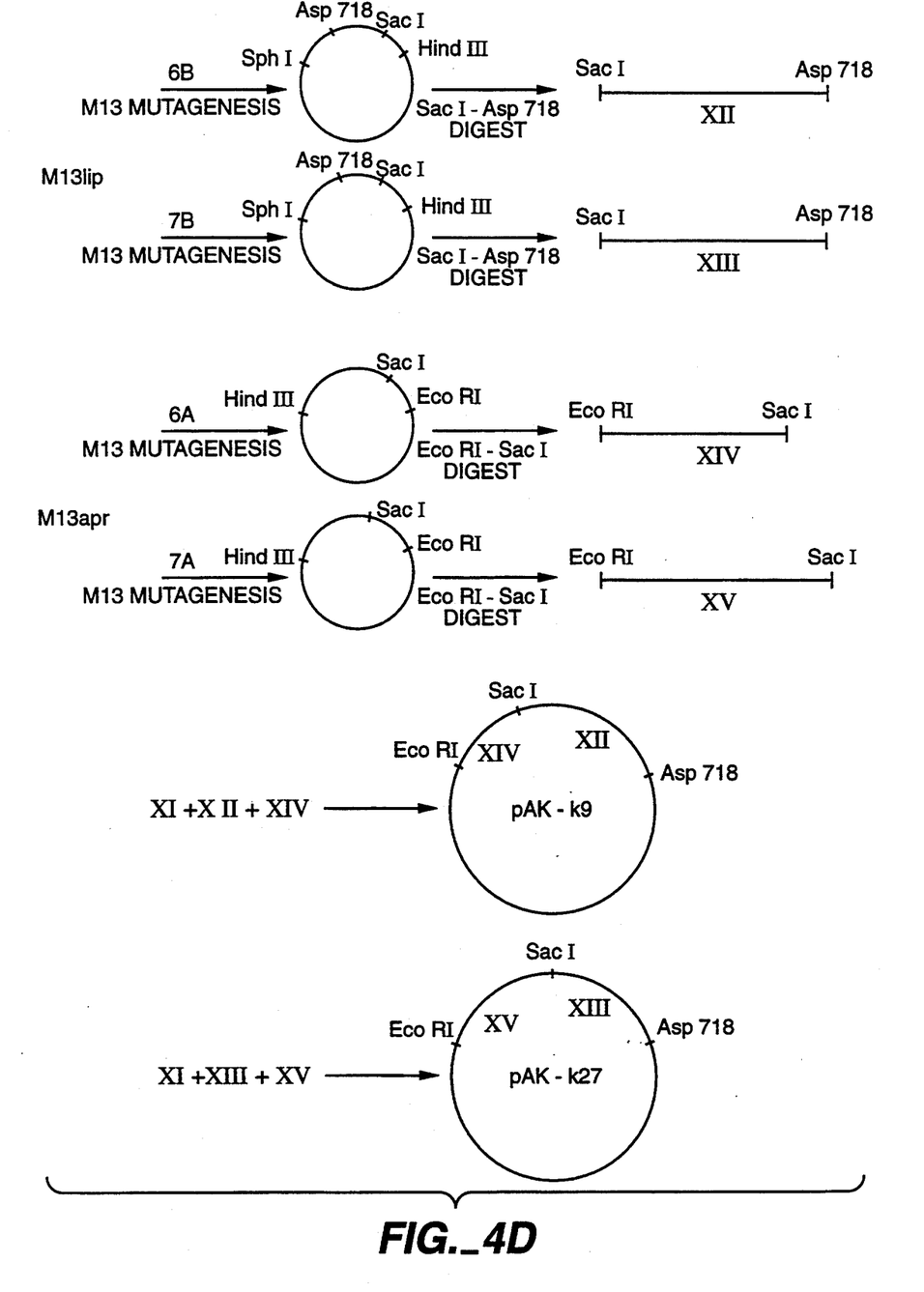
Figure 4E:
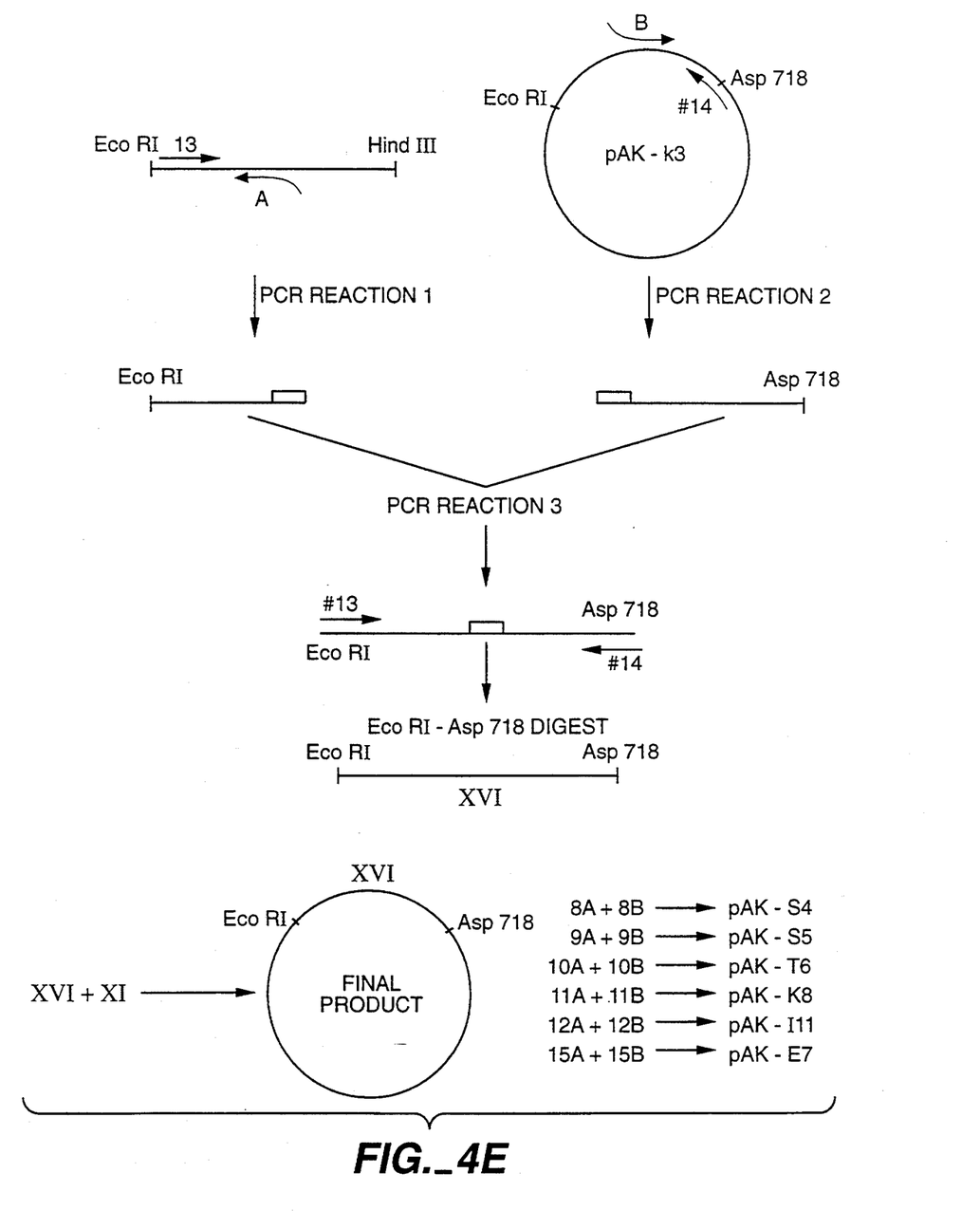
Figure 5:
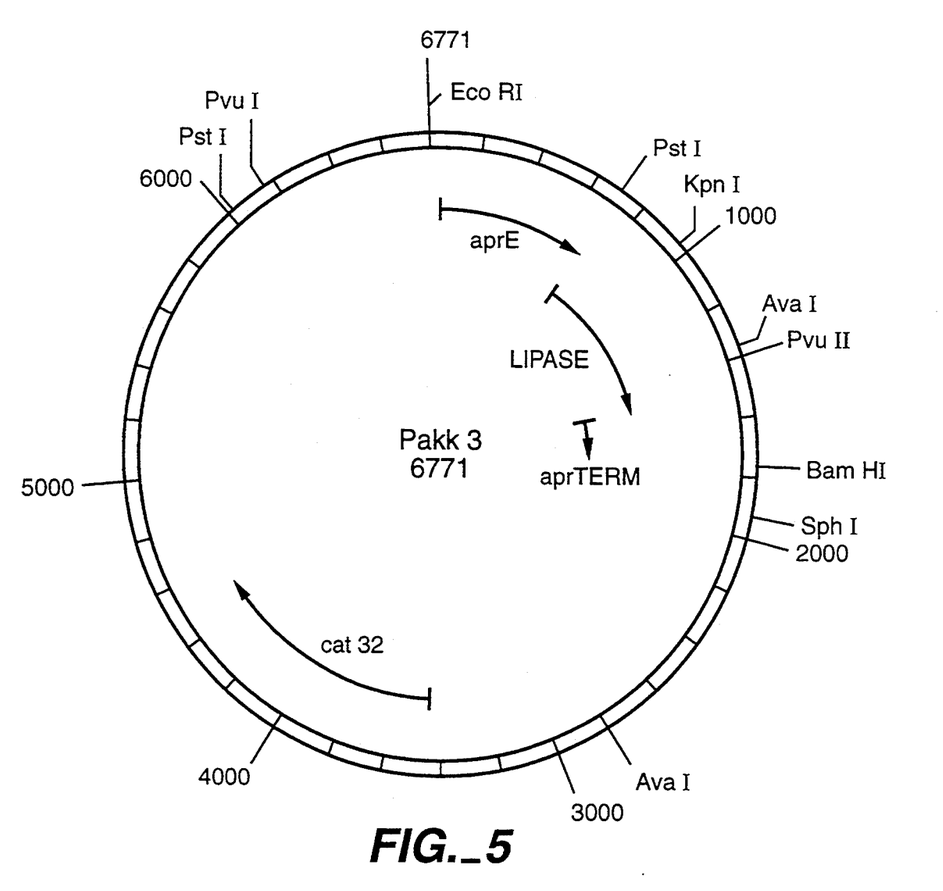
FIG. 5 shows the plasmid map of pAK-K3.

As shown in FIG. 3, the different fusions produced dramatically different expression levels. The relative production rates varied as much as 5 fold (K3/S4) and the best (K3) produced 5 fold better than the simple direct signal sequence junction hookup (A-1).

What is claimed is:

1. A process for expressing Pseudomonas lipase protein in a Bacillus organism, the process comprising:
   a) constructing a plasmid comprising a gene encoding the Pseudomonas lipase protein fused at its N-terminus to the codon corresponding to one of the first through ninth amino acids of a Pseudomonas pro-sequence, wherein said prosequence is attached to its native signal sequence;
   b) transforming the Pseudomonas organism with the plasmid of step a) under appropriate conditions to integrate the plasmid into the Pseudomonas chromosome;
   c) recovering the produced transformants and/or the expressed Pseudomonas lipase protein.

2. A process of claim 1 wherein the gram-positive host organism is *Bacillus subtilis*.

3. A process of claim 1 wherein the Bacillus prosequence and signal sequence are the *Bacillus subtilis* aprE prosequence and signal sequence.

4. A process of claim 1 further comprising a Bacillus promoter attached to the signal sequence.

5. A process of claim 4 wherein the promoter is the *Bacillus subtilis* aprE promoter.

6. A process of claim 1 wherein the gram-negative derived target protein is *Pseudomonas mendocina* lipase, ATCC 53552.

7. A process of claim 1 wherein the plasmid of step a) comprises a mature *Pseudomonas mendocina* lipase gene fused at its N-terminus to the codon corresponding to the third amino acid of the *Bacillus subtilis* aprE prosequence, wherein the prosequence is attached to the *Bacillus subtilis* aprE signal sequence.

8. A process of claim 1 wherein the plasmid of step a) comprises a mature *Pseudomonas mendocina* lipase gene fused at its N-terminus to the codon corresponding to the sixth amino acid of the *Bacillus subtilis* aprE prosequence.

9. The method according to claim 1, wherein a SacU(Hy) mutation is additionally introduced into the Bacillus organism.

10. The process according to claim 1, wherein said pro-sequence is the aprE pro-sequence.

11. Transformed Bacillus cells comprising DNA coding for a Pseudomonas lipase protein, wherein the DNA is fused at its N-terminus to a codon corresponding to the first through ninth amino acids of a Bacillus pro-sequence, wherein said pro-sequence is attached to its native signal sequence.

12. Transformed cells of claim 11 wherein the gram-positive host cells are *Bacillus subtilis*.

13. Transformed cells of claim 11 wherein the lipase is *Pseudomonas mendocina* lipase, ATCC 53552.

14. Transformed cells of claim 12 comprising heterologous DNA coding for a *Pseudomonas mendocina* lipase fused to a codon corresponding to one of the first through ninth amino acids of the *Bacillus subtilis* aprE prosequence, wherein the aprE prosequence is attached to the *Bacillus subtilis* aprE signal sequence.

15. Transformed cells of claim 14 wherein the DNA coding for the lipase is fused to the codon corresponding to the third amino acid of the *Bacillus subtilis* aprE prosequence.

16. Transformed cells of claim 14 wherein the DNA coding for the lipase is fused to the codon corresponding to the sixth amino acid of the *Bacillus subtilis* aprE prosequence.

17. The transformed cells according to claim 11, wherein the transformed cells additionally contain a SacU(Hy) mutation.

18. The transformed cells according to claim 11, wherein said pro-sequence is the aprE pro-sequence.

19. A recombinant DNA construct comprising a mature *Pseudomonas mendocina* lipase gene fused at its N-terminus to a codon corresponding to one of the first through ninth amino acids of a *Bacillus subtilis* aprE prosequence.

20. A plasmid containing the DNA construct of claim 19.

21. A recombinant DNA construct comprising a mature *Pseudomonas mendocina* lipase gene fused at its N-terminus to a codon corresponding to the third amino acid of a *Bacillus subtilis* aprE prosequence.

22. A plasmid containing the DNA construct of claim 21.

23. A recombinant DNA construct comprising a mature *Pseudomonas mendocina* lipase gene fused at its N-terminus to a codon corresponding to the sixth amino acid of a *Bacillus subtilis* aprE prosequence.

24. A plasmid containing the DNA construct of claim 23.

* * * * *

UNITED STATES PATENT AND TRADEMARK OFFICE
CERTIFICATE OF CORRECTION

PATENT NO. : 5,429,950
DATED : July 4, 1995
INVENTOR(S) : Power et al.

It is certified that error appears in the above-indentified patent and that said Letters Patent is hereby corrected as shown below:

Column 17:

At claim 1, lines 7, 10 and 12, change "Pseudomonas" to --Bacillus--;
Columns 17 and 18:
At claim 2, lines 1-2, and claim 12, lines 1-2, change "gram-positive host" to --Bacillus--.

Signed and Sealed this

Fourteenth Day of November, 1995

Attest:

BRUCE LEHMAN

Attesting Officer　　　Commissioner of Patents and Trademarks